(12) United States Patent
Suwa

(10) Patent No.: US 7,273,372 B2
(45) Date of Patent: Sep. 25, 2007

(54) DENTAL ARTICULATOR

(76) Inventor: Kenji Suwa, 16-24, Uenosaka 1-chome, Toyonaka-shi, Osaka (JP)

( * ) Notice: Subject to any disclaimer, the term of this patent is extended or adjusted under 35 U.S.C. 154(b) by 0 days.

(21) Appl. No.: 11/146,162

(22) Filed: Jun. 7, 2005

(65) Prior Publication Data

US 2005/0272000 A1    Dec. 8, 2005

(30) Foreign Application Priority Data

Jun. 7, 2004    (JP)    ............................. 2004-168308

(51) Int. Cl.
*A61C 11/00*    (2006.01)
(52) U.S. Cl. .............................. 433/64; 433/54; 433/57
(58) Field of Classification Search .................. 433/64, 433/54, 65, 63, 56, 57, 60, 61, 62
See application file for complete search history.

(56) References Cited

U.S. PATENT DOCUMENTS

| | | | | |
|---|---|---|---|---|
| 2,824,371 A | * | 2/1958 | Granger | 433/57 |
| 3,818,595 A | * | 6/1974 | Stuart | 433/57 |
| 4,439,150 A | * | 3/1984 | Edwardson | 433/56 |
| 4,445,855 A | * | 5/1984 | Hobo et al. | 433/59 |
| 4,496,319 A | * | 1/1985 | Steinbock | 433/57 |
| 4,687,442 A | * | 8/1987 | Wong | 433/63 |
| 4,721,463 A | * | 1/1988 | Lee | 433/54 |
| 4,764,113 A | * | 8/1988 | Hiranuma | 433/56 |
| 5,431,564 A | * | 7/1995 | Guichet | 433/56 |
| 6,287,113 B1 | * | 9/2001 | Nagata | 433/57 |
| 6,299,442 B1 | * | 10/2001 | Shiao et al. | 433/64 |
| 2002/0012896 A1 | * | 1/2002 | Nagata | 433/57 |

FOREIGN PATENT DOCUMENTS

JP    2000-42004    2/2000

* cited by examiner

*Primary Examiner*—Melba N. Bumgarner
*Assistant Examiner*—Jonathan Werner
(74) *Attorney, Agent, or Firm*—Wenderoth, Lind & Ponack, L.L.P.

(57) ABSTRACT

A dental articulator includes a lower jaw member, two pillars each extending vertically upwardly from the lower jaw member. The pillars each carry a ball, which correspond to a human mandibular condyle. The articulator further includes an upper jaw member disposed over the lower jaw member and carrying housings each provided on either side of a rear portion of said upper jaw member. Each of the balls is received in one of the housings so that the upper jaw member is vertically pivotable about the balls. Each housing includes a top wall coupled to the upper jaw member so as to be vertically movable relative to the upper jaw member while kept in contact with one of the balls and configured to be fixed to the upper jaw member at any position, and a rear wall coupled to the upper jaw member so as to be movable back and forth while kept in contact with one of the balls and configured to be fixed to the upper jaw member.

10 Claims, 6 Drawing Sheets

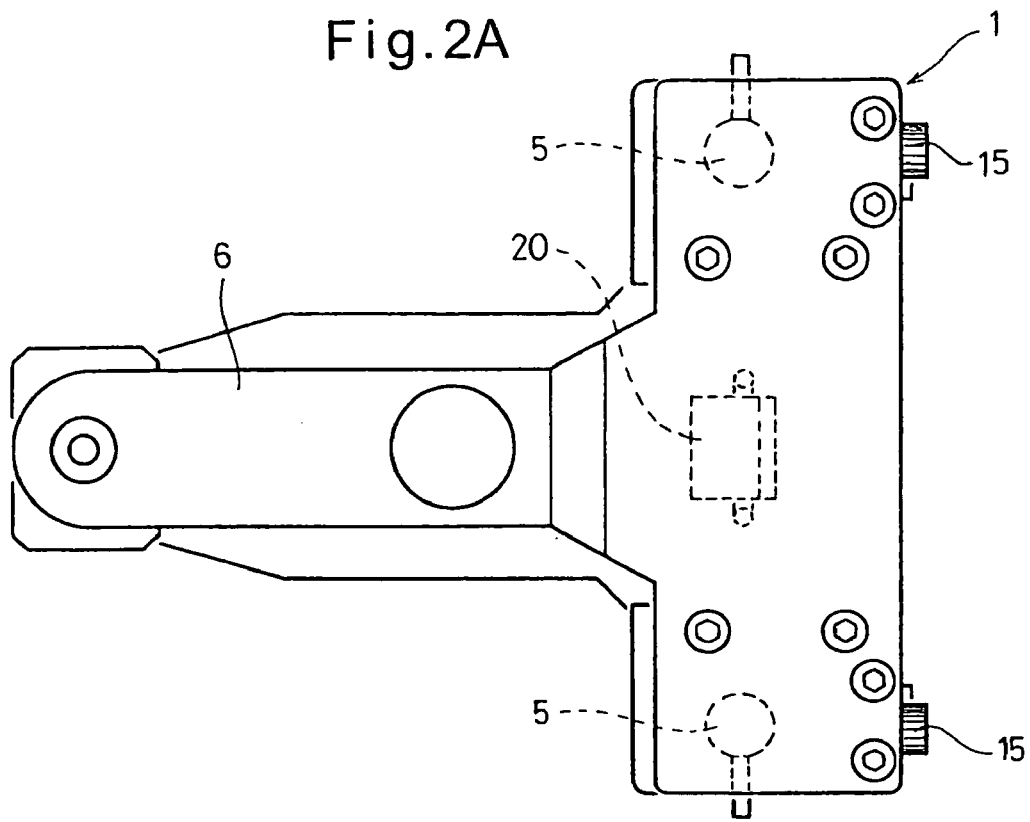
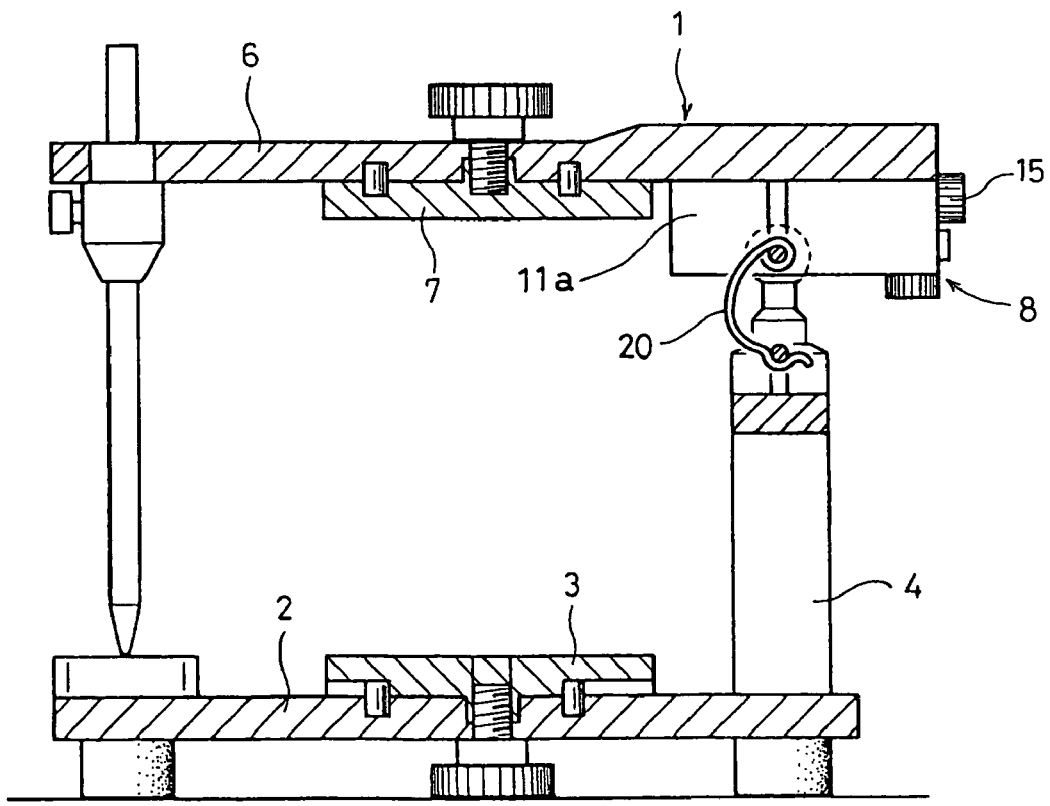

DENTAL ARTICULATOR

BACKGROUND OF THE INVENTION

This invention relates to a dental articulator which can reproduce the positions of the mandibular condyles of a patient suffering from malocclusion and thus makes it possible for a dentist to treat the malocclusion by referring to the positions of the mandibular condyles reproduced on the articulator.

Articulators, which are used to manufacture dentures, are available in many types. One such articulator is called an arcon type mean value articulator, which comprises a lower jaw member, and two pillars each extending vertically upwardly from either side of the rear portion of the lower jaw member. The pillars each carry a ball, which corresponds to a mandibular condyle, at the top end thereof. An upper jaw member is disposed over the lower jaw member and carries housings each provided on either side of the rear portion thereof. Each of the balls is received in one of the housings so that the upper jaw member is vertically pivotable about the balls. In some of such articulators, the height of the balls are adjustable, and the upper and lower jaw members are movable back and forth relative to each other.

Such an articulator further includes a lower mounting disk mounted on the lower jaw member for mounting a lower jaw model, and an upper mounting disk mounted on the upper jaw member for mounting an upper jaw model. Such an articulator was originally developed to reproduce the movement of human jaws, more specifically the movement of the mandibular condyles by pivoting the upper jaw member until the teeth of the upper jaw model abuts the teeth of the lower jaw mode, thereby treating any malocclusion (see JP patent publication 2000-42004).

The term "centric occlusion" refers to the optimum position of the mandibular condyles. The term "habitual occlusion" refers to the position of the mandibular condyles when the opposed teeth of the upper and lower jaws are all stably in contact with each other.

If the centric occlusion and the habitual occlusion do not coincide, temporomandibular joint syndrome may result.

Many diagnostic techniques are known for checking if the centric occlusion and the habitual occlusion coincide. The most recent technique is to check if the mandibular condyles are in their optimal positions when the opposed teeth of the upper and lower jaws are all stably in contact with each other. For this purpose, three-dimensional X-rays and MRI are typically used.

But with this technique, it is impossible to measure the distance between the optimum positions of the mandibular condyles and their positions at the habitual occlusion.

A dentist uses such a dental articulator in preparing prostheses and also to treat temporomandibular joint syndrome.

But even though the optimal positions of the mandibular condyles are known, as long as this information cannot be reproduced on the articulator, it is impossible to use this information for the treatment of temporomandibular joint syndrome.

Some dental articulators have their balls as the mandibular condyles arranged to be vertically movable and their upper and lower jaw models movable back and forth relative to each other. In this arrangement, since the balls, which correspond to the mandibular condyles, vertically move, even though their optimum positions are known, such data cannot be reproduced on the articulator. Thus, it is impossible to diagnose and/or treat temporomandibular joint syndrome.

An object of the invention is to provide a dental articulator which can reproduce data on the optimum positions of mandibular condyles of a patient, whereby temporomandibular joint syndrome can be diagnosed or treated based on such data.

SUMMARY OF THE INVENTION

According to the present invention, there is provided a dental articulator comprising a lower jaw member, two pillars each extending vertically upwardly from either side of a rear portion of the lower jaw member, the pillars each carrying a ball at a top end thereof, and an upper jaw member disposed over the lower jaw member and carrying housings each provided on either side of a rear portion of the upper jaw member, each of the balls being received in one of the housings. The upper jaw member is vertically pivotable about an axis defined by the ball. Each of the housings comprises a top wall coupled to the upper jaw member so as to be vertically movable relative to the upper jaw member while kept in contact with one of the balls and configured to be fixed to the upper jaw member at any position, and a rear wall coupled to the upper jaw member so as to be movable back and forth while kept in contact with the one of the balls and configured to be fixed to the upper jaw member.

Each of the housings may further comprise a first setscrew extending through the top wall and threadedly engaged in the upper jaw member, and a second setscrew extending through the rear wall and threadedly engaged in the upper jaw member, whereby the top wall and the rear wall can be fixed to the upper jaw member by selectively tightening the first and second setscrews, the top wall having a horizontal bottom surface.

The top wall is coupled to an end wall of the upper jaw member through a vertical guide comprising a groove and a rib. The first setscrew extends through the end wall and is threadedly engaged in the top wall so that the top wall is movable vertically by about 4 to 5 mm and can be fixed in position at any desired point within this vertical range by tightening the first setscrew.

The rear wall is provided under the horizontal bottom surface of the top wall and mounted to the end wall through a horizontal guide comprising a groove and a rib so as to be slidable back and forth relative to the end wall 11. The second setscrew extends through the rear wall and is threadedly engaged in the end wall. Thus, the rear wall is slidable back and force by about 4-5 mm relative to the end wall 11 and can be fixed in position at any desired point within the back-and-force movable range by tightening the second setscrew. The top wall and the rear wall are arranged so as not to interfere with each other.

An arcuate leaf spring engages the rear portion of the upper jaw member and a crossbar extending between the pillars to keep the upper jaw member in position while biasing it rearwardly.

With this arrangement, the upper jaw member can be vertically pivotable with the balls fixed at positions corresponding to the optimum positions of the mandibular condyles of the patient. Thus, data on the optimum positions of the mandibular condyles of the patient can be reproduced on the articulator. Based on this data, it is possible to diagnose and/or treat temporomandibular joint syndrome.

BRIEF DESCRIPTION OF THE DRAWINGS

Other features and objects of the present invention will become apparent from the following description made with reference to the accompanying drawings, in which:

FIG. 2A is a plan view of the same;

FIG. 2B is a front view in vertical section of the same;

DETAILED DESCRIPTION OF THE PREFERRED EMBODIMENTS

Figure 1:
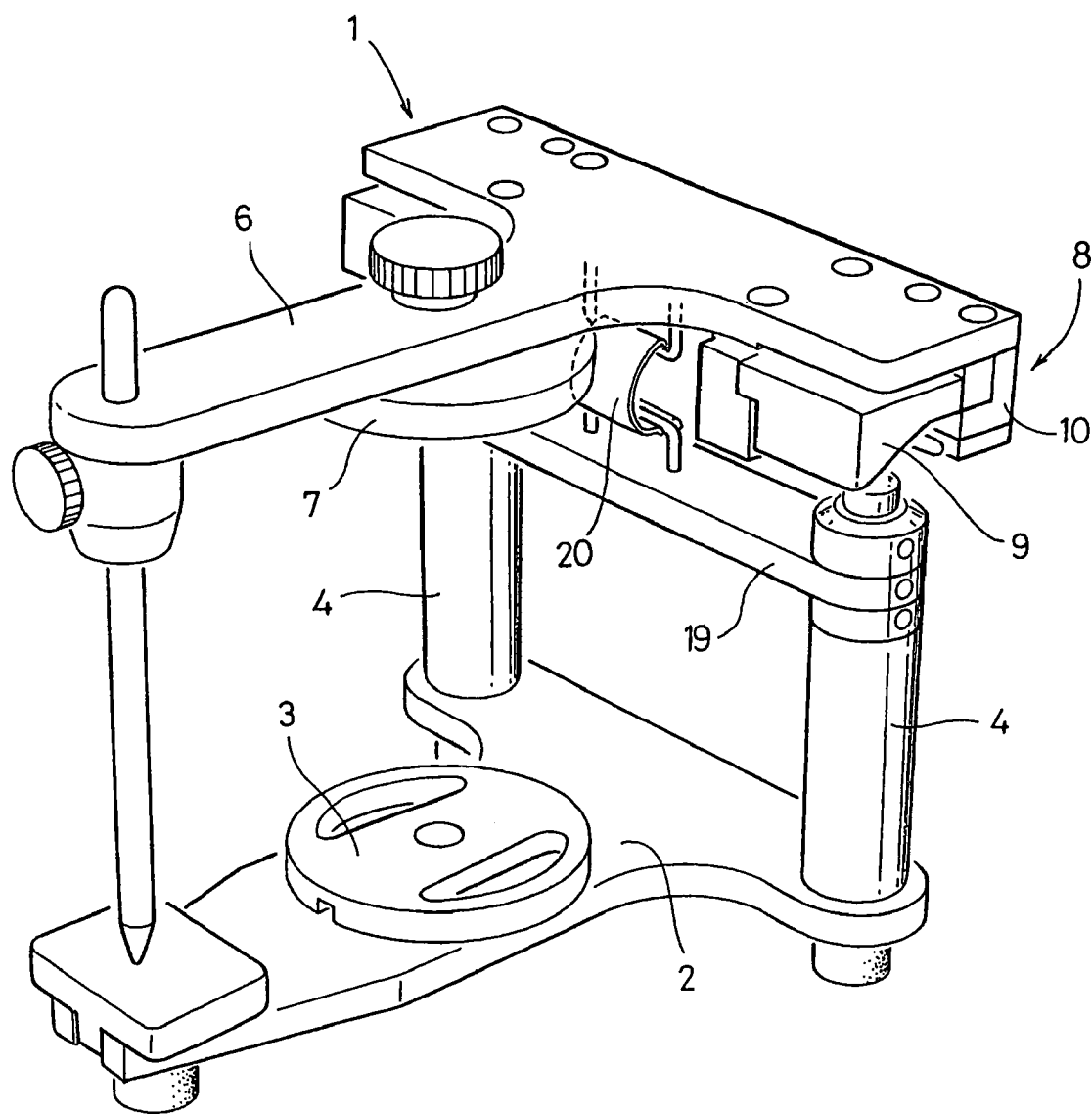
FIG. 1 is a perspective view of the dental articulator embodying the invention.
Figure 3:
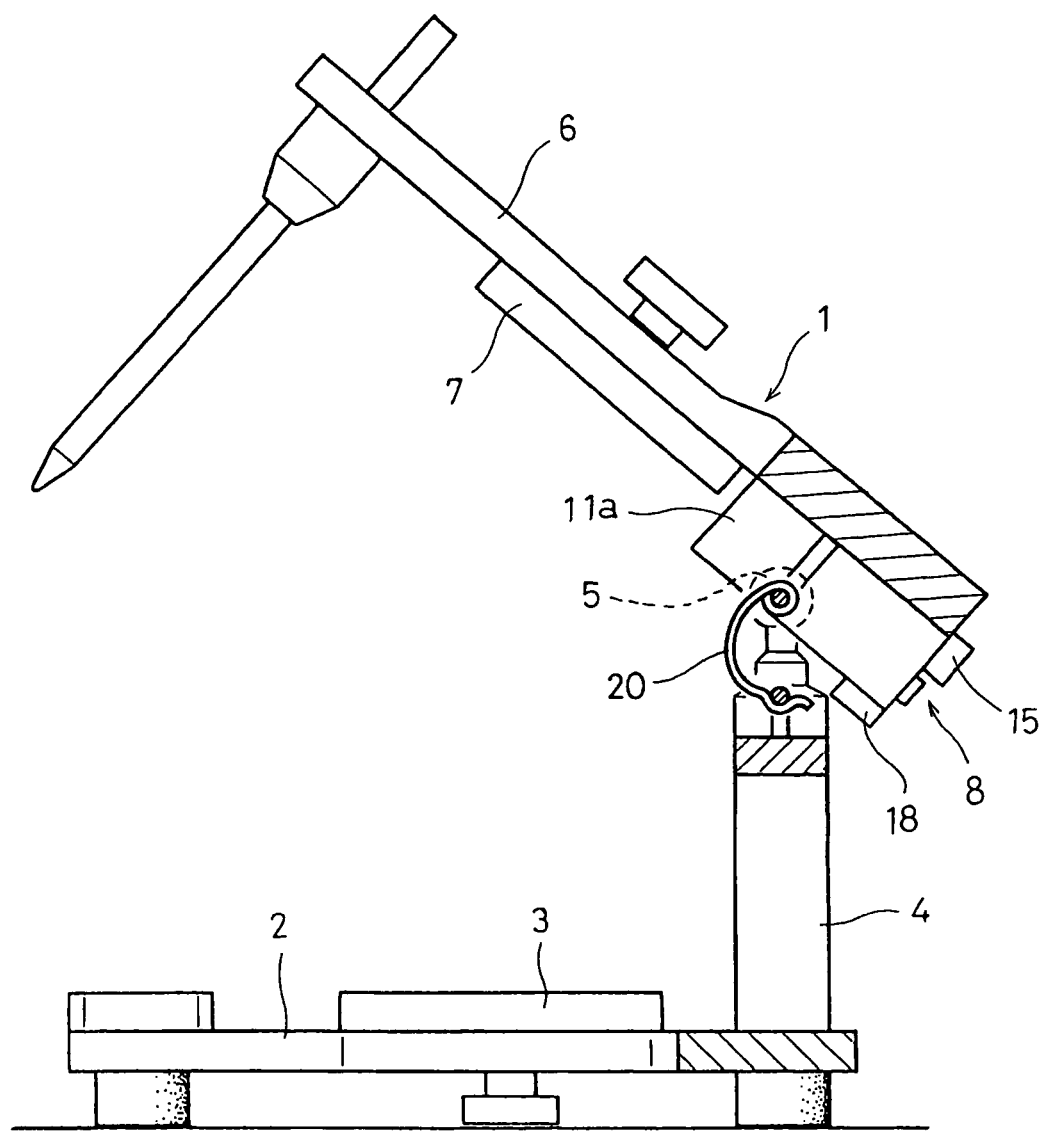
FIG. 3 is a view similar to FIG. 2B, showing its open state.

Now referring to the drawings, the articulator 1 embodying the invention includes a lower jaw member 2 having substantially the shape of the letter T as viewed from above. A lower mounting disk 3 is mounted on the top surface of the lower jaw member 2 at its center. Pillars 4 extend vertically from both rear arms of the T-shaped lower jaw member 2. Each pillar 4 carries at its top end a ball 5 as a mandibular condyle.

The articulator 1 further includes an upper jaw member 6 having the shape of the letter T as viewed from above. At the free ends of the rear arms thereof, the upper jaw member 6 carries housings 8 in which are received the respective balls 5 so that the upper jaw member 6 is pivotable vertically about the balls 5 (i.e. about a pivot axis defined by a straight line connecting the balls 5). The upper jaw member 6 also carries on its bottom surface an upper mounting disk 7 at its center.

Figure 6:
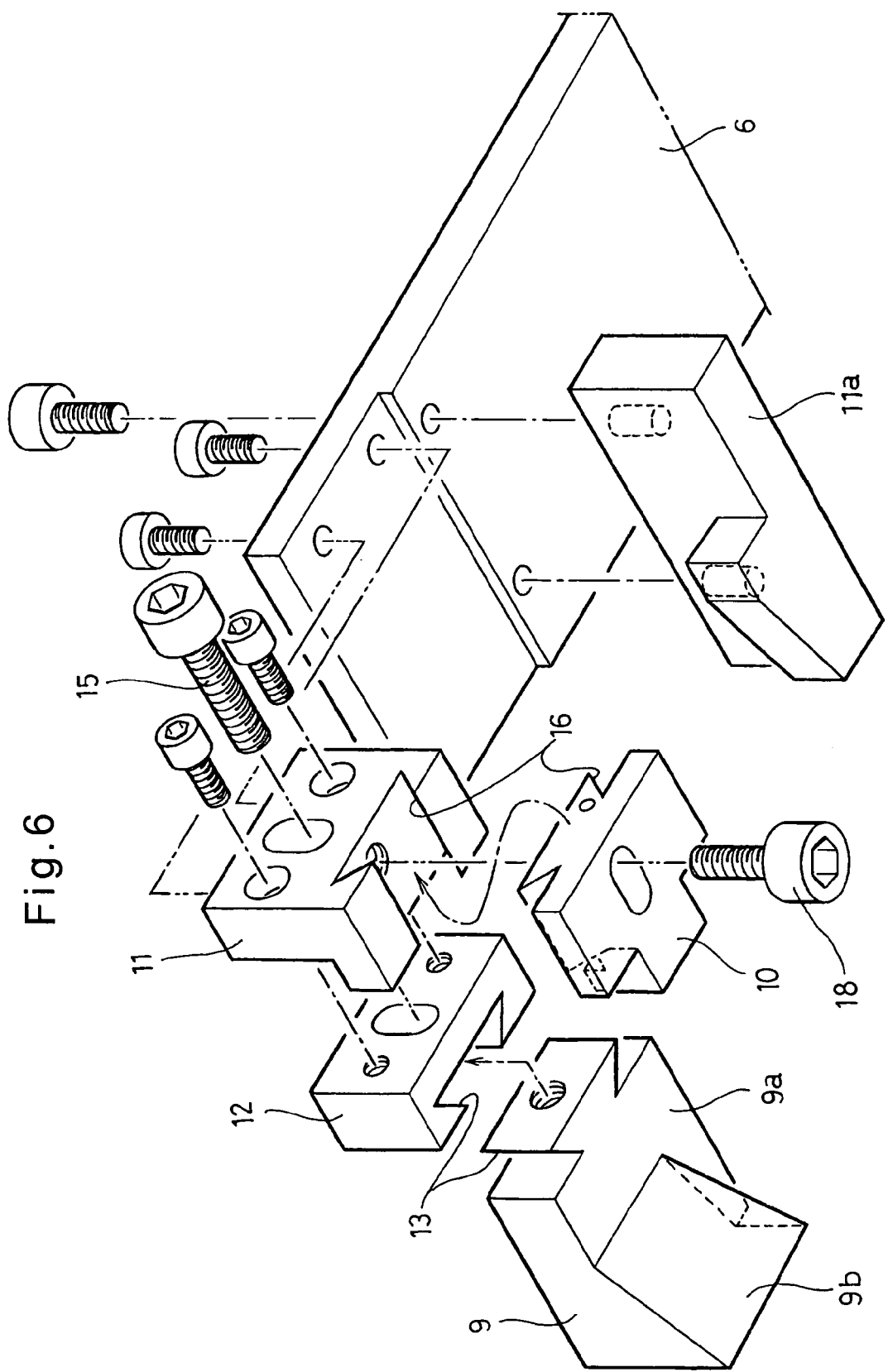
FIG. 6 is an exploded perspective view (as viewed from below) of one of the housings.

Each housing 8 comprises an end wall 11 and a side wall 11a both secured to the bottom of the upper jaw member 6 (see FIG. 6), a top wall 9 which is vertically movably mounted to the end wall 11 and adapted to abut the top of the ball 5, and a rear wall 10 which is mounted to the end wall 11 so as to be slidable back and forth and adapted to abut the rear of the ball 5. Thus, the upper jaw member 6 is movable vertically and back and forth relative to the balls 5.

Figure 4A:
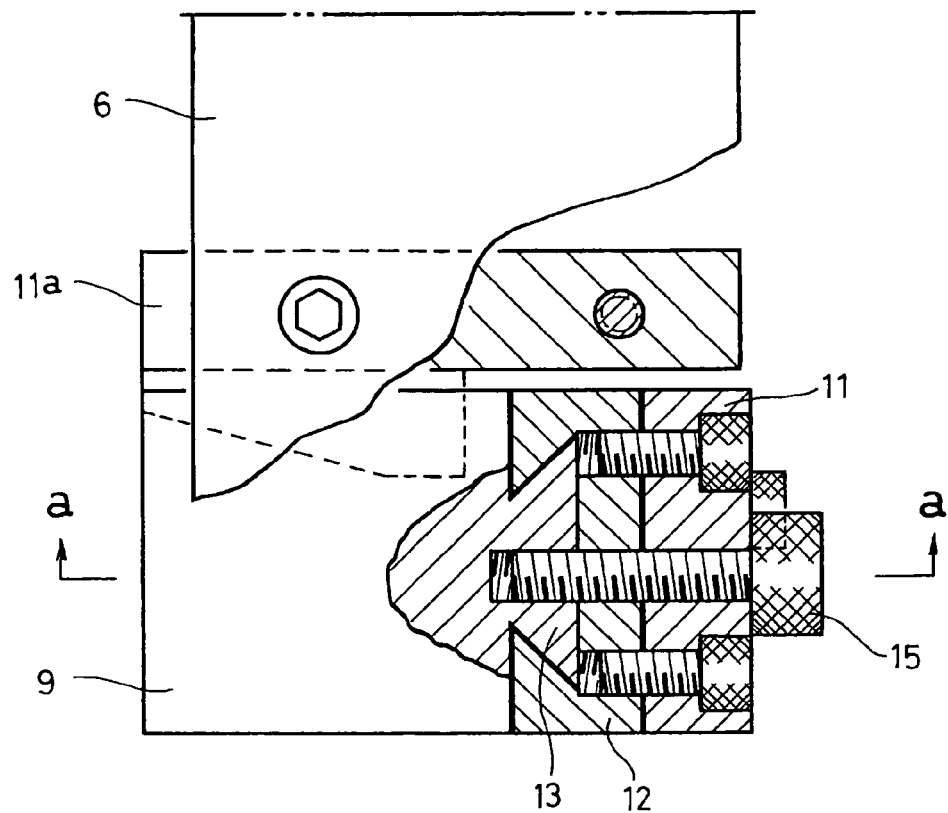
FIG. 4A is a partially cutaway plan view of one of a pair of housings of the articulator of FIG. 1.

As best shown in FIG. 4A, the top wall 9 is coupled to the end wall 11 through a vertical guide 13 comprising a groove formed in the front face of an intermediate member 12 fixed to the end wall 11, and a rib formed on the rear end of the top wall 9 and vertically slidably received in the groove. A setscrew (threaded bolt) 15 extends through vertically elongated holes 14 formed in the end wall 11 and the intermediate wall 12 and is threadedly engaged in a threaded hole formed in the rib of the top wall 9. Thus, the top wall 9 is movable vertically by about 4 to 5 mm and can be fixed in position at any desired point within this vertical range by tightening the setscrew 15.

The top wall 9 has a bottom surface comprising a rear horizontal surface 9a and a front inclined surface 9b inclined obliquely downwardly toward its front end. The top wall 9 shown is a one-piece member, but the front portion including the inclined surface 9b may be prepared separately from and later secured to the remaining rear portion, i.e. the portion including the horizontal surface 9a.

Figure 4B:
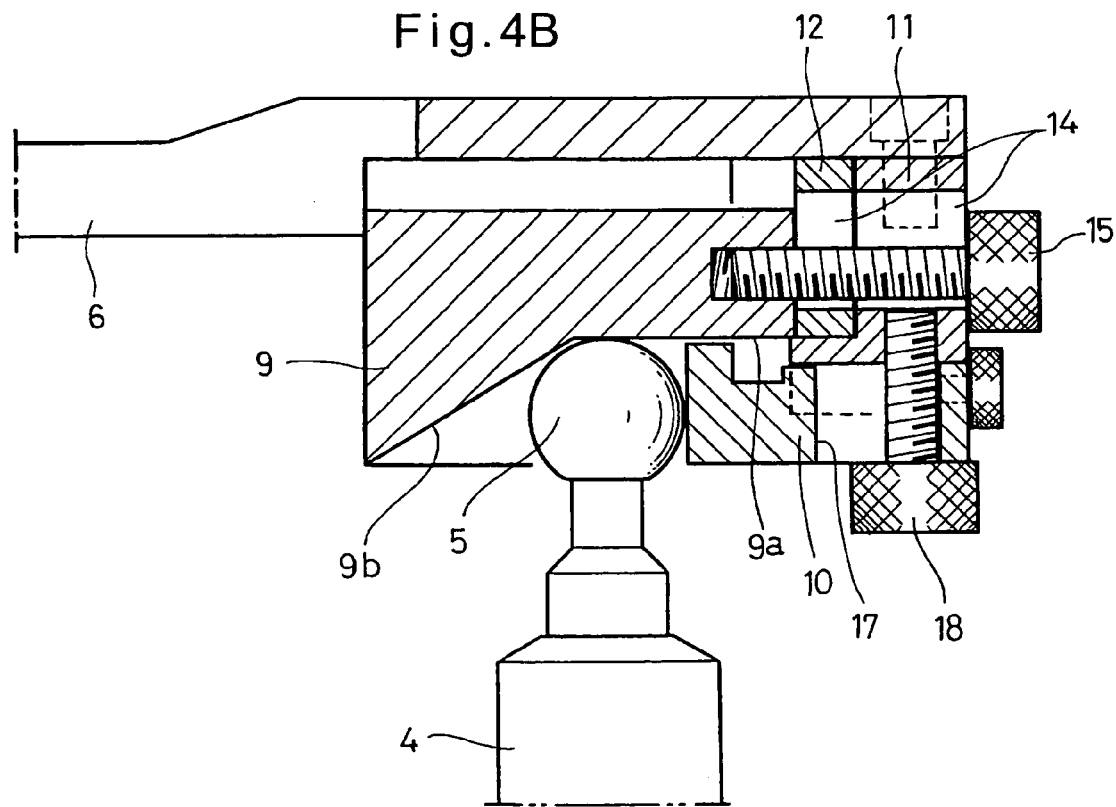
FIG. 4B is a sectional view taken along line a-a of FIG. 4A.
Figure 5:
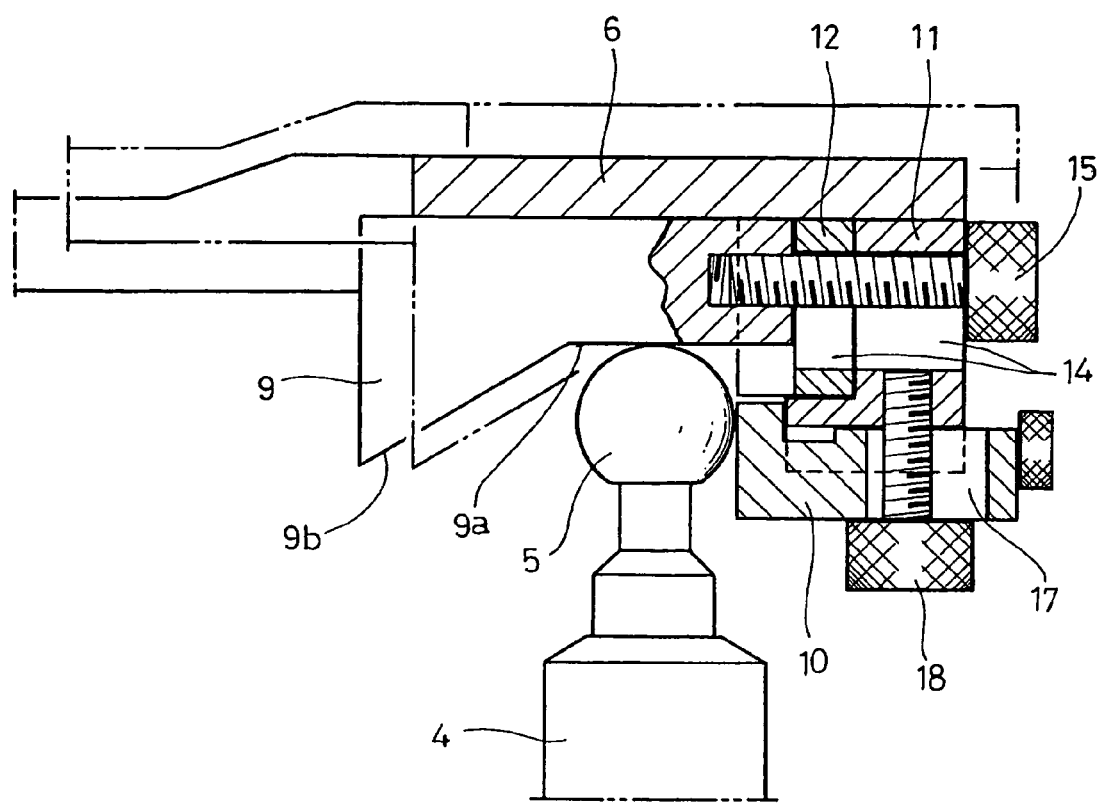
FIG. 5 is a partially cutaway, enlarged front view of a portion of the articulator, showing how a top wall and a rear wall of one of the housings move.

As best shown in FIG. 4B, the rear wall 10 is mounted to the bottom of the end wall 11 through a horizontal guide 16 (FIG. 6) comprising a groove formed in the bottom of the rear wall 10 and a rib formed on the top of the rear wall 10 and received in the groove so as to be slidable back and forth relative to the end wall 11. A setscrew 18 extends through an elongated hole 17 formed in the rear wall 10 and is threadedly engaged in a threaded hole formed in the end wall 11. Thus, the rear wall 10 is slidable back and force by about 4-5 mm relative to the end wall 11 and can be fixed in position at any desired point within the back-and-force movable range by tightening the setscrew 18. The top wall 9 and the rear wall 10 are arranged so as not to interfere with the horizontal movement of the rear wall 10 and the vertical movement of the top wall 9, respectively.

Graduations are provided along the boundary between the intermediate wall 12 and the top wall 9 to indicate the vertical displacement of the top wall 9. Similar graduations are provided along the boundary between the end wall 11 and the rear wall 10 to indicate the back-and-forth displacement of the rear wall 10. An arcuate leaf spring 20 engages the rear portion of the upper jaw member 6 and a crossbar 19 extending between the pillars 4 to keep the upper jaw member 6 in position while biasing it rearwardly.

This articulator is used as follows. First, the tooth/jaw configuration of a patient is acquired using a face bow. Based on the tooth/jaw configuration thus acquired, an upper jaw model is prepared and mounted on the upper mounting disk 7, which is mounted on the upper jaw member 6, such that the jaw model and the balls 5 are arranged in the same positional relationship as the corresponding parts in the patient's mouth.

In this state, the top wall 9 and the rear wall 10 of each housing 8 are moved until they abut the corresponding ball 5, and the setscrews 15 and 18 are tightened to fix the top wall 9 and the rear wall 10 in position. The elongated holes 14 and 17 are formed such that in this initial state, the setscrews 15 and 18 are substantially in the middle of the respective holes 14 and 17.

Then, the patient's dental impressions are obtained using e.g. three sheets of bite wax having thicknesses of 5, 8 and 11 mm, respectively, by having the patient lightly bite the respective sheets.

A lower jaw model is then prepared and mounted on the lower mounting disk 3 on the lower jaw member 2 with one of the bite wax sheets disposed between the upper and lower jaw models such that the biting surfaces of the teeth on both upper and lower jaws will snugly fit in the dental impressions on the bite wax sheet.

This sheet is then removed and the remaining two sheets are inserted one by one into between the upper and lower jaw models to confirm that the biting surfaces of the teeth on both upper and lower jaw models fit in the dental impressions on either of the remaining two sheets, too.

If the biting surfaces of the teeth of both of the upper and lower jaw models fit in the impressions on any of the three bite wax sheets, this generally means that any point of the patient's jaws follows a substantially completely circular path when the patient opens or closes his or her mouth between the closed position and the position in which the upper and lower jaws separate from each other by 25 mm. (This is called "Postert's banana".) This is because the balls 5, which correspond to the patient's mandibular condyles, are not movable.

However, if the patient is suffering from temporomandibular joint syndrome, some of the opposed teeth of the upper and lower jaw models may remain out of contact with each other when the other opposed teeth are in contact with each other.

In such a case, when the setscrews 15 and 18 are loosened, since the upper jaw model becomes movable relative to the lower jaw model, the upper jaw model will move, relative to the balls 5, to a stable position where all of the opposed teeth of the upper and lower jaw models contact each other. In this state, the setscrews 15 and 18 are tightened again, and graduations are read to determine the displacements of the top wall 9 and the rear wall 10, which correspond to the vertical and back-and-force displacements of the upper jaw model, which in turn correspond to the vertical and back-and-force displacements of the patient's mandibular condyles. Thus, based on the displacements of the top wall 9 and the rear wall 10 determined by reading the graduations, it is possible to treat temporomandibular joint syndrome.

The invention claimed is:

1. A dental articulator comprising:
   a lower jaw member;
   two pillars each extending vertically upwardly from either side of a rear portion of said lower jaw member, said pillars each carrying a ball at a top end thereof; and
   an upper jaw member disposed over said lower jaw member and carrying housings each provided on either side of a rear portion of said upper jaw member, each of said balls being received in one of said housings such that said upper jaw member is pivotable about a pivot axis defined by a straight line connecting said balls;
   wherein each of said housings comprises a top wall coupled to said upper jaw member so as to be movable relative to said upper jaw member along a straight line extending in a first direction perpendicular to said pivot axis while kept in contact with a respective one of said balls, and a rear wall coupled to said upper jaw member so as to be movable along a straight line extending in a second direction perpendicular to both said first direction and said pivot axis while kept in contact with said respective one of said balls;
   wherein, for each of said housings, each of said top wall and said rear wall is configured to be fixed to said upper jaw member against movement relative to said upper jaw member when in a desired position;
   wherein each of said housings further includes an intermediate part fixed to said upper jaw member;
   wherein, for each of said housings, said top wall and said rear wall are coupled to said upper jaw member through said intermediate part; and
   wherein, for each of said housings, said intermediate part has a first groove extending in said first direction, and said top wall has a rib engaged in said first groove of said intermediate part so as to be movable in said first direction.

2. The dental articulator of claim 1, wherein for each of said housings, said intermediate part has a second groove extending in said second direction, and said rear wall has a rib engaged in said second groove of said intermediate part so as to be movable in said second direction.

3. The dental articulator of claim 2, wherein
   for each of said housings, said intermediate part has a first elongated hole formed therethrough, said first elongated hole being elongated in said first direction, said top wall has a first threaded hole formed therein, and a first threaded bolt is inserted through said first elongated hole and threaded into said first threaded hole such that, by tightening of said threaded bolt in said first threaded hole, said top wall can be fixed in a desired position relative to said intermediate part and said upper jaw member.

4. The dental articulator of claim 3, wherein
   for each of said housings, said rear wall has a second elongated hole formed therethrough, said second elongated hole being elongated in said second direction, said intermediate part has a second threaded hole formed therein, and a second threaded bolt is inserted through said second elongated hole and threaded into said second threaded hole such that, by tightening of said threaded bolt in said second threaded hole, said rear wall can be fixed in a desired position relative to said intermediate part and said upper jaw member.

5. The dental articulator of claim 4, wherein
   for each of said housings, each of said first and second grooves of said intermediate part has a trapezoidal cross section, with a width thereof narrowing toward a surface opening thereof, and said ribs of said top wall and said rear wall have trapezoidal cross sections complementary to those of said first and second grooves, respectively.

6. The dental articulator of claim 5, wherein
   for each of said housings, said top wall has a bottom surface including a rear horizontal surface portion and a front inclined surface portion inclined upwardly in a rearward direction.

7. The dental articulator of claim 2, wherein
   for each of said housings, each of said first and second grooves of said intermediate part has a trapezoidal cross section, with a width thereof narrowing toward a surface opening thereof, and said ribs of said top wall and said rear wall have trapezoidal cross sections complementary to those of said first and second grooves, respectively.

8. A dental articulator comprising:
   a lower jaw member;
   two pillars each extending vertically upwardly from either side of a rear portion of said lower jaw member, said pillars each carrying a ball at a top end thereof; and
   an upper jaw member disposed over said lower jaw member and carrying housings each provided on either side of a rear portion of said upper jaw member, each of said balls being received in one of said housings such that said upper jaw member is pivotable about a pivot axis defined by a straight line connecting said balls;
   wherein each of said housings comprises a top wall coupled to said upper jaw member so as to be movable relative to said upper jaw member along a straight line extending in a first direction perpendicular to said pivot axis while kept in contact with a respective one of said balls, and a rear wall coupled to said upper jaw member so as to be movable along a straight line extending in a second direction perpendicular to both said first direction and said pivot axis while kept in contact with said respective one of said balls;
   wherein, for each of said housings, each of said top wall and said rear wall is configured to be fixed to said upper jaw member against movement relative to said upper jaw member when in a desired position;
   wherein each of said housings further includes an intermediate part fixed to said upper jaw member;
   wherein, for each of said housings, said top wall and said rear wall are coupled to said upper jaw member through said intermediate part; and wherein, for each of said housings, said intermediate part has a groove extending in said second direction, and said rear wall has a rib engaged in said groove of said intermediate part so as to be movable in said second direction.

9. The dental articulator of claim 8, wherein
for each of said housings, said groove of said intermediate part has a trapezoidal cross section, with a width thereof narrowing toward a surface opening thereof, and said rib of said rear wall has trapezoidal cross section complementary to that of said groove.

10. A dental articulator comprising:
a lower jaw member;
two pillars each extending vertically upwardly from either side of a rear portion of said lower jaw member, said pillars each carrying a ball at a top end thereof; and
an upper jaw member disposed over said lower jaw member and carrying housings each provided on either side of a rear portion of said upper jaw member, each of said balls being received in one of said housings such that said upper jaw member is pivotable about a pivot axis defined by a straight line connecting said balls;
wherein each of said housings comprises a top wall coupled to said upper jaw member so as to be movable relative to said upper jaw member along a straight line extending in a first direction perpendicular to said pivot axis while kept in contact with a respective one of said balls, and a rear wall coupled to said upper jaw member so as to be movable along a straight line extending in a second direction perpendicular to both said first direction and said pivot axis while kept in contact with said respective one of said balls;

wherein, for each of said housings, each of said top wall and said rear wall is configured to be fixed to said upper jaw member against movement relative to said upper jaw member when in a desired position;
wherein each of said housings further includes an intermediate part fixed to said upper jaw member;
wherein, for each of said housings, said top wall and said rear wall are coupled to said upper jaw member through said intermediate part;
wherein, for each of said housings, said intermediate part has a first elongated hole formed therethrough, said first elongated hole being elongated in said first direction, said top wall has a first threaded hole formed therein, and a first threaded bolt is inserted through said first elongated hole and threaded into said first threaded hole such that, by tightening of said threaded bolt in said first threaded hole, said top wall can be fixed in a desired position relative to said intermediate part and said upper jaw member; and
wherein, for each of said housings, said rear wall has a second elongated hole formed therethrough, said second elongated hole being elongated in said second direction, said intermediate part has a second threaded hole formed therein, and a second threaded bolt is inserted through said second elongated hole and threaded into said second threaded hole such that, by tightening of said threaded bolt in said second threaded hole, said rear wall can be fixed in a desired position relative to said intermediate part and said upper jaw member.

* * * * *